US009211283B2

(12) United States Patent
Langer et al.

(10) Patent No.: US 9,211,283 B2
(45) Date of Patent: *Dec. 15, 2015

(54) NANOPARTICLE CARRIER SYSTEMS BASED ON HUMAN SERUM ALBUMIN FOR PHOTODYNAMIC THERAPY

(75) Inventors: Klaus Langer, Münster (DE); Matthias Wacker, Nidderau (DE); Beate Röder, Falkensee (DE); Annegret Preuss, Berlin (DE); Volker Albrecht, Bergholz Rehbrücke (DE); Susanna Gräfe, Jena (DE); Arno Wiehe, Berlin (DE); Hagen von Briesen, Hunstetten (DE); Karin Löw, Saarlouis (DE); Sylvia Wagner, Neunkirchen (DE)

(73) Assignee: Biolitec Pharma Marketing Ltd, Labuan (MY)

( * ) Notice: Subject to any disclaimer, the term of this patent is extended or adjusted under 35 U.S.C. 154(b) by 302 days.

This patent is subject to a terminal disclaimer.

(21) Appl. No.: 12/941,350

(22) Filed: Nov. 8, 2010

(65) Prior Publication Data

US 2011/0142948 A1 Jun. 16, 2011

Related U.S. Application Data

(60) Provisional application No. 61/285,902, filed on Dec. 11, 2009.

(51) Int. Cl.
*A61K 9/51* (2006.01)
*A61K 31/409* (2006.01)
(Continued)

(52) U.S. Cl.
CPC .............. *A61K 31/409* (2013.01); *A61K 9/5169* (2013.01); *A61K 41/0071* (2013.01)

(58) Field of Classification Search
CPC ............ A61K 31/409; A61K 41/0071; A61K 9/5169; A61K 9/5153; A61K 33/20
See application file for complete search history.

(56) References Cited

U.S. PATENT DOCUMENTS 6,007,791 A * 12/1999 Coombes et al. ............ 424/1.29
2001/0051189 A1* 12/2001 Alonso Fernandez et al. .............................. 424/499

(Continued)

OTHER PUBLICATIONS

Langer et al., "Optimization of the preparation process for human serum albumin (HSA) nanoparticles," International Journal of Pharmaceutics, 257 (2003) pp. 169-180.*

(Continued)

*Primary Examiner* — Aradhana Sasan
(74) *Attorney, Agent, or Firm* — B J Associates; Bolesh J. Skutnik (57) ABSTRACT

Compositions, which are stable in storage, and a method of production of pharmaceutical based nanoparticulate formulations for photodynamic therapy comprising a hydrophobic photosensitizer, human serum albumin (HSA) and stabilizing agent are provided. These nanoparticulate formulations provide therapeutically effective amounts of photosensitizer (PS) for parenteral administration. In particular, tetrapyrrole derivatives can be used as photosensitizers whose efficacy and safety are enhanced by such nanoparticulate formulations. A method of preparing the HSA-based nanoparticles under sterile conditions is also provided. In one of the preferred embodiments of the present invention temoporfin, a hydrophobic PS, is formulated as a nanoparticle for parenteral administration. The formulations are useful for treating hyperplasic and neoplasic conditions, inflammatory problems, and more specifically to target tumor cells.

11 Claims, 6 Drawing Sheets

(51) Int. Cl.
 *A61K 33/20* (2006.01)
 *A61K 41/00* (2006.01)

(56) References Cited

U.S. PATENT DOCUMENTS

2003/0103995 A1* 6/2003 Hamblin et al. ............ 424/185.1
2005/0215524 A1* 9/2005 Albrecht et al. ................ 514/78
2009/0304803 A1* 12/2009 Hasan ........................... 424/497
2010/0273803 A1* 10/2010 Grafe et al. .................... 514/250
2011/0275686 A1* 11/2011 Langer et al. ................. 514/410

OTHER PUBLICATIONS

Lin et al., "Preparation of Sub-100 nm Human Serum Albumin Nanospheres Using a pH-Coacervation Method," Journal of Drug Targeting, 1993, vol. 1, pp. 237-243.*

* cited by examiner

NANOPARTICLE CARRIER SYSTEMS BASED ON HUMAN SERUM ALBUMIN FOR PHOTODYNAMIC THERAPY

DOMESTIC PRIORITY UNDER 35 USC 119(e)

This application claims the benefit and priority of U.S. Provisional Application Ser. No. 61/285,902 filed Dec. 11, 2009, entitled "NANOPARTICLE CARRIER SYSTEMS BASED ON HUMAN SERUM ALBUMIN FOR PHOTODYNAMIC THERAPY (PDT)" by Klaus Langer et al., which is incorporated by reference herein.

BACKGROUND OF THE INVENTION

1. Field of the Invention

The present invention relates to drug formulation of hydrophobic photosensitizer. In particular, the invention relates to nanoparticle formulations containing hydrophobic photosensitizers, to their method of preparation and to their use in photodynamic therapy for destruction of unwanted cells or tissues, and more particularly for photodynamic tumor therapy, using intravenous administration.

2. Invention Disclosure Statement

Photodynamic therapy (PDT) is one of the most promising new techniques now being explored for use in a variety of medical applications and particularly is a well-recognized treatment for the destruction of tumors. Photodynamic therapy uses light and a photosensitizer (a dye) to achieve its desired medical effect. A large number of naturally occurring and synthetic dyes have been evaluated as potential photosensitizers for photodynamic therapy. Perhaps the most widely studied class of photosensitizers are the tetrapyrrolic macrocyclic compounds. Among them, especially porphyrins and chlorins have been tested for their PDT efficacy.

Porphyrins are macrocyclic compounds with bridges of one carbon atom joining pyrroles to form a characteristic tetrapyrrole ring structure. There are many different classes of porphyrin derivatives including those containing dihydropyrrole units. Chlorins and bacteriochlorins are porphyrin derivative, which contain one dihydro- or two dihydro-pyrrole units respectively.

Chlorins have their absorption spectrum in the red and near-infrared region of the electromagnetic spectrum. As light of longer wavelength penetrates deeper into the tissue it is possible to treat more expanded and deeper tumors, if the PDT is employed for tumor therapy. Chlorins can either be derived from natural sources or from total synthesis.

Chlorins from natural compounds are obtained by derivatizing chlorophylls or bacteriochlorophylls. Methods to prepare chlorins and bacteriochlorins by total synthesis generally use porphyrins, and then are converted to a chlorin or bacteriochlorin system. This conversion step can e.g. be performed by the reduction with in situ generated diimine or by dihydroxylation leading to dihydro- or dihydroxy-substituted chlorins or bacteriochlorins, respectively Raymond Bonnett et al., in their patent No. EP 00337601B1, disclose a method for preparation of photosensitizers by reduction of corresponding porphyrins. Total synthesis of temoporfin (chemical name: (m-tetrahydroxyphenyl-chlorin))-a chlorin, is disclosed. Temoporfin (Foscan®) is successfully used in Europe as a photosensitizer for the PDT treatment of head and neck cancer. Similarly patent application WO 09613504A1 by David Dolphin et al. and patent application WO 00061584A1 by Jill Maclpine et al. teach reduction method of preparation of novel photosensitizer having improved properties.

Porphyrins can be either directly used as photosensitizers for PDT or as a precursors for the synthesis of chlorins by subjecting pyrrole and aldehyde(s) to a condensation reaction. Suitable methods for this condensation have long been known in the art.

The use of PDT for the treatment of various types of disease has been limited due to the inherent features of photosensitizers (PS). These include their high cost, extended retention in the host organism, substantial skin phototoxicity, low solubility in physiological solutions reducing their usefulness for intravascular administration thus leading to thromboembolic accidents, and lower targeting effectiveness. These disadvantages, particularly of PS in the prior art, had led to the administration of very high doses of a photosensitizer, which dramatically increase the possibility of accumulation of the photosensitizer in normal tissues and the accompanying risk of affecting normal sites.

Efforts to reduce cost and to decrease background toxicity have been underway but are unrelated to the developments of the present invention. Work to improve solubility in physiological solutions, effects of skin photo-toxicity, retention in host organism and to a lesser extent targeting effectiveness are the areas where the present invention provides new and non-obvious improvements on the use of PDT to treat various neoplasia, hyperplasia and related diseases.

Most substances successfully employed for photodynamic tumor therapy are lipophilic substances, which due to their inherent low solubility in water need to be formulated in a proper way. Therefore, there is a great need for new formulations of tetrapyrrole-based photosensitizers to enhance their uptake in the body and their bioavailability.

Nanoparticles are intensively investigated as carriers for lipophilic drug substances (N. P. Preatorius, T. K. Mandal, Engineered Nanoparticles in Cancer Therapy, *Recent Patents on Drug Delivery & Formulation*, 2007, 1, 37-51; M. N. V. Ravi Kumar, Engineered Nanoparticles in Cancer Therapy, *J. Pharm. Pharmaceut. Sci.*, 2000, 3, 234-258). A nanoparticle formulation of the anti-cancer drug Paclitaxel based on human serum albumin (HSA) has been approved by regulatory authorities in Europe and the USA.

In PCT publication No. WO 01/21174 A1, Anand Burman et al. disclose a method for preparing a pharmaceutical formulation of paclitaxel an anti-cancer drug and its derivatives and analogy entrapped into nanoparticles of co-polymeric micelles. The nanoparticle is formed by a polymerization method; yet mostly polymerization reaction based method requires the use of large amount of organic solvent or unsafe stabilizer like surfactant that could results in toxic side effects.

In the prior art, nanoparticles are used for encapsulation/entrapment/adsorption of macromolecules, other therapeutic agents and diagnosing agent used for biomedical application. Majority of the nanoparticles are prepared from polymeric material, and use for their preparation large amount of organic solvents and toxic surfactants which need to be removed completely to avoid any possible side effects in patients. One of the problems that is encountered with some nanoparticulate compositions is the solubilization and subsequent recrystallization of the component crystalline drug particles. Crystal growth and particle aggregation in nanoparticulate active agent preparations are highly undesirable. The presence of large crystals in the nanoparticulate active agent composition may cause undesirable side effects, especially when the preparation is in an injectable formulation. Larger particles formed by particle aggregation and recrystallization can also interfere with blood flow, causing pulmonary embolism and death.

Nanoparticles in general are solid colloidal particles ranging in size from 10 nm to 1000 nm and are used in some drug delivery systems. Nanoparticles consist of macromolecular materials in which the active principle is dissolved, entrapped or encapsulated, and/or to which the active principle is absorbed or attached. Many different sorts of nanoparticle material have been investigated, such as quantum dots, silica-based nanoparticles, photonic crystals, liposomes, nanoparticles based on different polymers of natural and synthetic origin, and metal-based nanoparticles. Nanoparticles are diverse both in their shape and composition.

Most interesting as carrier systems for photosensitizers are nanoparticles that consist of biocompatible materials. Such carrier systems could significantly improve the treatment regimen of photodynamic therapy. A carrier system with such known high biocompatibility is e.g. human serum albumin (HSA). HSA material has successfully been formulated as nanoparticles (see. K. Langer, et al. in. *Intl. J. Pharm.*, 2007, 347, 109-117).

There are few examples of protein-based nanoparticles as carriers for water insoluble pharmacologically active agents known in the art.

In U.S. Pat. No. 5,916,596, Desai et al. disclose a composition and method for delivery of hydrophobic anti-cancer drug paclitaxel in the form of suspended particle coated with protein. It discloses protein-based nanoparticles of size less than 200 nm diameter for drug delivery and these are sterile-filtered. Smaller size nanoparticles have greater aggregation during storage. This known art describes suspended drug particles coated with protein, which acts as a stabilizing agent, but this patent is unrelated to the present invention.

The application of a nanoparticle formulation for parenteral administration in clinical practice requires that the sterility of the formulation according to pharmacopoeial specifications can be assured. Also, for a clinical application it is desirable that the formulation can be freeze dried and later be reconstituted in an aqueous medium. Sterility of nanoparticle photosensitizer formulations involving HSA is challenging because of the lability of the nanoparticle matrix material as well as the lability of the photosensitizer. Conventional methods of sterilization (autoclaving, use of ethylene oxide, gamma-irradiation) are incompatible with the present invention photosensitizer formulations (see. K. A. Athanasiou, et al. in, *Biomaterials*, 1996, 17, 93-102; C. Volland, et al., *J. Contr. Rel.*, 1994, 31, 293-305).

Eric Allemann et al. in their patent application WO 03097096A1 disclose compositions and methods for parenteral or local delivery of photosensitizer using bridgeable nanoparticles containing polyester polymers. It also discloses preparation and use of such nanoparticles. The nanoparticles are sterilized using filtration methods. Nevertheless, this method has its drawbacks and is not generally compatible with the nanoparticles that are subject of the present invention. Pore size for sterile filtration is usually no greater than 0.22 μm (≥220 nm) whereas nanoparticles of the present invention populate essentially the whole size range between 100 and 500 nm. Therefore, sterile filtration has its drawbacks and is generally incompatible with the nanoparticles that are subject of the present invention.

In particular, it is difficult to develop sterile nanoparticle formulations and nanoparticle formulations suitable for freeze drying in the case of photosensitizers of the present invention which are of the chlorin or bacteriochlorin type (i.e. tetrapyrroles carrying one or two dihydro-pyrrole units), because such systems are especially sensitive to oxidation and photo-chemical modifications induced by the handling conditions that are often used for nanoparticle preparation (Y. Hongying, et al. *Dyes Pigm.* 1999, 43, 109-117; C. Hadjur, at al., *J. Photochem. Photobiol. B: Biology,* 1998, 45, 170-178; R. Bonnett, et al. in *J. Chem. Soc. Perkin Trans.* 2, 1999, 325-328). These photosensitizers of the chlorin or bacteriochlorin type which possess one or two dihydro-pyrrole units, respectively, differ significantly in their chemical and physical behaviour from their corresponding porphyrins (R. Bonnett, et al. in *J. Chem. Soc. Perkin Trans.* 2, 1999, 325-328; R. Bonnett, et al. *J. Porphyrins Phthalocyanines,* 2001, 5, 652-661).

The known prior art on HSA-based nanoparticles used as carriers for photosensitizers does not address problems related to sterility and freeze-drying of HSA-based nanoparticles and the investigated photosensitizers are less problematic in this respect because of their more stable chemical structure.

Hydrophobic photosensitizers need to be formulated using suitable carriers due to their inherent low solubility in water. Therefore, there is a great need for new formulations of tetrapyrrole-based photosensitizers to enhance their uptake in the body and their bioavailability. The use of PDT for the treatment of various types of disease has been limited due to the inherent features of photosensitizers (PS). These include their high cost, extended retention in the host organism, substantial skin phototoxicity, low solubility in physiological solutions reducing their usefulness for intravascular administration thus leading to thromboembolic accidents, and lower targeting effectiveness.

The present invention obviates the above discussed problems seen in the formulation of hydrophobic photosensitizers by providing a pharmaceutical compatible nanoparticle made of natural material as a drug delivery system and for parenteral administration. Present invention also provides method to improve the bioavailability, stability and solubility of sensitive hydrophobic PS.

OBJECTIVES AND BRIEF SUMMARY OF THE INVENTION

It is an objective of the present invention to address the problem of suitable nanoparticle formulations of hydrophobic photosensitizers for photodynamic therapy that meet the necessities for a parenteral administration in clinical practice.

It is another objective of the present invention to provide nanoparticle pharmaceutical formulations of hydrophobic photosensitizers for photodynamic therapy based on biocompatible HSA material.

It is yet another objective of the present invention to provide nanoparticle formulations for hydrophobic photosensitizers of the tetrapyrrole type, namely chlorins and bacteriochlorins, based on human serum albumin (HSA) and a stabilizing agent, preferably glutaraldehyde, formaldehyde or thermal treatment.

It is a further objective of the present invention to be able to freeze dry the sterilized HSA-based nanoparticles and to reconstitute in aqueous medium, when required.

It is still a further objective of the present invention to provide methods for the use of nanoparticle photosensitizer formulations based on EISA in PDT.

Briefly stated, the present invention provides compositions, which are stable in storage, and a method of production of pharmaceutical based nanoparticulate formulations for photodynamic therapy comprising a hydrophobic photosensitizer, human serum albumin (HSA) and stabilizing agent. These nanoparticulate formulations provide therapeutically effective amounts of photosensitizer (PS) for parenteral administration. In particular, tetrapyrrole derivatives can be used as photosensitizers whose efficacy and safety are enhanced by such nanoparticulate formulations. A method of preparing the HSA-based nanoparticles under sterile conditions is also provided. In one of the preferred embodiments of the present invention temoporfin, a hydrophobic PS, is formulated as a nanoparticle for parenteral administration. The formulations are useful for treating hyperplasic and neoplasic conditions, inflammatory problems, and more specifically to target tumor cells.

The above and other objects, features and advantages of the present invention will become apparent from the following description read in conjunction with the accompanying drawings.

BRIEF DESCRIPTION OF FIGURES AND TABLES

Table I: Physico-chemical characteristics of 5,10,15,20-tetrakis(m-hydroxyphenyl)-porphyrin (mTHPP)-loaded HSA nanoparticles (mean±S.D.; n=6)

Table II: Fluorescence lifetime of mTHPP in ethanol and in form of HSA nanoparticles mTHPP-loaded in the presence of 0.75% and 2.0% soluble HSA in aqueous solutions Table III: Singlet oxygen generation and triplet parameters of Rose Bengal in ethanol and in form of HSA nanoparticles mTHPP-loaded in the presence of 0.75% and 2.0% soluble HSA in aqueous solutions Table IV: Physico-chemical characteristics of 5,10,15,20-tetrakis(m-hydroxyphenyl)-chlorin (mTHPC)-loaded HSA nanoparticles (mean±S.D.; n=3)

FIG. 4 A-D Analysis of the cell uptake of HSA-based nanoparticles with the photosensitizer 5,10,15,20-tetrakis(3-hydroxyphenyl)-porphyrin (mTHPP)

FIG. 5 A-D Analysis of the cell uptake of HSA-based nanoparticles with the photosensitizer 5,10,15,20-tetrakis(3-hydroxyphenyl)-chlorin (mTHPC).

FIG. 6 A-D Dark toxicity and the phototoxicity effects on Jurkat cells in 5 different samples after different incubation times.

DETAILED DESCRIPTION OF PREFERRED EMBODIMENTS

Present invention provides protein based nanoparticle pharmaceutical formulations for photosensitizers suitable for parenteral application. Protein based nanoparticles are biodegradable, non-toxic, stable for long duration, non-antigenic and promotes cellular uptake when compared to prior art polymeric based nanoparticles. It also provides a suitable method to prepare protein based nanoparticles for such sensitive compounds as chlorins and bacteriochlorins, which are hydrophobic photosensitizers (PS) that generally have problems in solubility and stability, creating major formulation obstacles particularly for parenteral administration.

The present invention also provides methods to prepare pharmaceutical formulations of photosensitizer-containing nanoparticles using photosensitizers preferably selected primarily from the group of chlorin and bacteriochlorin types. The methods of the present invention can also be used with variety of other known hydrophobic PS in the art.

Methods of use are provided, as well, for hydrophobic photosensitizer formulations based on HSA nanoparticles for clinical use in PDT. The nanoparticle based formulation is used in order to render hydrophobic PS soluble for intravenous administration. The methods of use comprise the administration of the PS-entrapped nanoparticles, their accumulation in the target tissue and the activation of the photosensitizer by light of a specific wavelength. The administration is preferably by parenteral means such as, but not limited to, intravenous injection. Nanoparticles are better for intravenous delivery compared to other delivery systems because the tiniest capillaries are in the 5-6 µm range.

The therapeutic uses of the HSA-based nanoparticle pharmaceutical formulations include, but are not limited to dermatological disorders, ophthalmologic disorders, urological disorders, and inflammatory conditions such as arthritis. More preferably are uses for treating tumor tissues, neoplasia, hyperplasia and related conditions.

Materials Used for the Preparation of the Photosensitizer-Loaded Nanoparticles

1. Human Serum Albumin (HSA):

Human Serum Albumin (HSA) is most abundant protein in human blood plasma. It is soluble and monomeric. The albumin, used here, is preferably from human sources or a recombinant form of human serum albumin (rHSA). HSA, a plasma protein has a distinct edge over other materials used for nanoparticles preparation as they are biodegradable and easy to prepare in defined sizes. Moreover, they can carry reactive groups such as thiol, amino, and carboxylic groups making them suitable for ligand binding and surface modification. Drug entrapped HSA can be easily metabolized by proteases enzyme and drug loading can be quantified.

HSA to be used for the preparations underlying the present invention was obtained from Sigma-Aldrich (purity 96-99% by agarose gel electrophoresis). The product was tested negative for HIV I and HIV II, HCV, and HbsAg. The protein was provided in lyophilized form.

2. Photosensitizers:

The photosensitizers used in the present invention are preferably tetrapyrroles of the chlorin and bacteriochlorin type, i.e. dihydro-porphyrins and tetrahydro-porphyrins respectively. Such photosensitizers can either be derived from natural sources or by total synthesis. The total synthesis of chlorins and bacteriochlorins can be performed by first synthesizing the porphyrin and then transforming it to a chlorin or bacteriochlorin system.

The chlorins and bacteriochlorins to be used with the present invention have the following preferred structures:

mTHPC mTHPD-OH wherein:
R¹ is: H or OH
R² to R⁵ are substituents either in the meta- or para-position of the phenyl ring with R² to
R⁵ independently of one another chosen from a group of substituents consisting of: —OH, —COOH, —NH₂, —COOX, —NHX, OX, —NH—Y—COOH, or —CO—Y—NH₂.
wherein:
X is a polyethyleneglycol-residue with $(CH_2CH_2O)_nCH_3$ with n=1-30 or a carbohydrate moiety
Y is peptides or oligopeptides wherein n=1-30.
Ring D has the structure:

Specifically preferred chlorins to be formulated in nanoparticles according to the present invention have the structure:

The nanoparticles prepared by the methods disclosed below have a predictable size and uniformity (in size distribution). Nanoparticles are prepared in an aseptic manufacturing process. Preferred HSA-based nanoparticles have a mean size less than 500 nm in diameter. The term "diameter" is not intended to mean that the nanoparticles have necessarily a spherical shape. The term refers to the approximate average width of the nanoparticles.

The nanoparticles need to be free of any toxic material for clinical use, therefore the nanoparticles are sterilized usually by different known means in the art such as autoclaving, use of ethylene oxide, and gamma-irradiation. These conventional methods of sterilization are incompatible, however, with the photosensitizer formulations of the present invention. An alternative, for such chemically and thermally sensitive materials, is the sterile filtration through membrane filters of a defined size. In the present invention nanoparticles, as required for medical applications, are prepared under complete sterile conditions.

In a specifically preferred embodiment of the present invention the HSA-based nanoparticles have a mean particle size less than 500 nm and the photosensitizer is temoporfin, 5,10,15,20-tetrakis(3-hydroxyphenyl)-chlorin (mTHPC). In another embodiment of the present invention, the HSA-based nanoparticles have a mean particle size less than 500 nm and the photosensitizer is 2,3-dihydroxy-5,10,15,20-tetrakis(3-hydroxyphenyl)-chlorin (mTHPD-OH). In still another embodiment of the present invention 5,10,15,20-tetrakis(m-hydroxyphenyl)-porphyrin (mTHPP) is used as photosensitizer.

The nanoparticles of the present invention may be dehydrated for improved stability on storage. The preferred method of dehydration is freeze-drying or lyophilisation. Optionally, a lyoprotectant may be used as an additive to improve the stability during the freeze-drying and during reconstitution in an aqueous medium (Anhorn, M. G., Mahler, H.-C., Langer, K., Freeze-drying of human serum albumin (HSA)-nanoparticles with different excipients. *Int. J. Pharm.* 2008, 363, 162-169.).

The HSA-based nanoparticles of the present invention were prepared by a desolvation procedure. In principle, protein desolvation of an aqueous HSA solution was induced by the controlled addition of a hydrophilic organic solvent such as ethanol, methanol, isopropanol, and (or) acetone. As an alternative the addition of concentrated polyethylene glycol solutions (≥20% in water; preferred embodiment 40%) can be used for desolvation. The resulting nanoparticles were stabilised by thermal processes or by using bifunctional aldehydes (i.e. glutaraldehyde) or formaldehyde.

The adsorption of the photosensitizer onto the preformed nanoparticles was performed in the presence of dissolved albumin. Drug loaded nanoparticles can be freeze dried in the presence of cryoprotective agents including, but not limited to glucose, trehalose, sucrose, sorbitol and mannitol and the like.

In the present invention the therapeutically effective concentration of the photosensitizer is about 10 to 50 µg per milligram of HSA nanoparticle, which corresponds to a particle content of 5-25 mg/ml in water suspension, typically 8 mg/ml. Drug incorporation in HSA nanoparticles can be performed by HSA desolvation in the presence of the photosensitizer and the use of polyethylene glycol as desolvating agent. The entire process of nanoparticle preparation was carried out under aseptic conditions.

The present invention is further illustrated by the following examples, but is not limited thereby.

EXAMPLE 1A

Preparation and Characterization of HSA-based Nanoparticles with the Photosensitizer 5,10,15,20-tetrakis(m-hydroxyphenyl)-porphyrin (mTHPP); Adsorptive Binding to Particle Surface (see Table I)

Human serum albumin (HSA) based nanoparticles were prepared by a desolvation method. In principle, 100 mg HSA was dissolved in 1 ml of 10 mM sodium chloride solution. The pH was adjusted to 8 and the solution was pre-filtered through a 0.22 µm filtration unit (Schleicher and Schüll, Dassel, Germany). This filtration process is sufficient to remove essentially all bacteria. Nanoparticles were formed by continuous addition of 4.0 ml ethanol under permanent stirring (380 rpm) at room temperature. A defined amount of ethanol is added at a rate of 1 ml/min using a pumping device (Ismatec IPN, Glattbrugg, Switzerland). After completion of protein desolvation, 57.76 µL of 8% aqueous glutaraldehyde solution was added to stabilize the resulting protein nanoparticles by chemical cross linking. The glutaraldehyde concentration used corresponds to 100% stoichiometric cross linking of the amino groups in 100 mg HSA. Particles were then stirred for 1 hour and purified by 3 cycles of centrifugation at 20,817×g, for 10 min, and the sediment was redispersed in 1.0 ml water. Redispersion step was performed in an ultrasonic bath for 5 min. The nanoparticle content was determined by microgravimetry and was adjusted to 15.0 mg/ml.

Drug Loading

Figure 1:
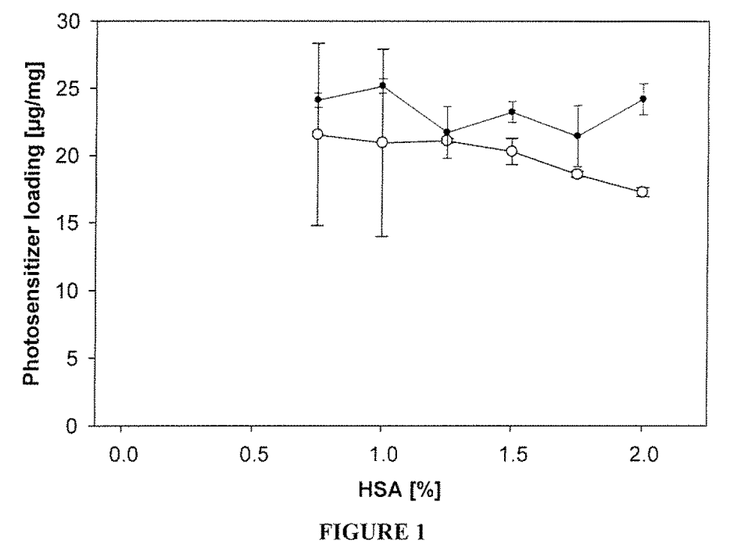
FIG. 1 Drug loading of HSA nanoparticles incubated with 5,10,15,20-tetrakis(m-hydroxyphenyl)-porphyrin (mTHPP) (○, mean±S.D.; n=6) and 5,10,15,20-tetrakis(m-hydroxyphenyl)chlorin (mTHPC) (●, mean±S.D.; n=6) depending on the concentration of dissolved HSA (0.75%-2.0%).
Figure 2:
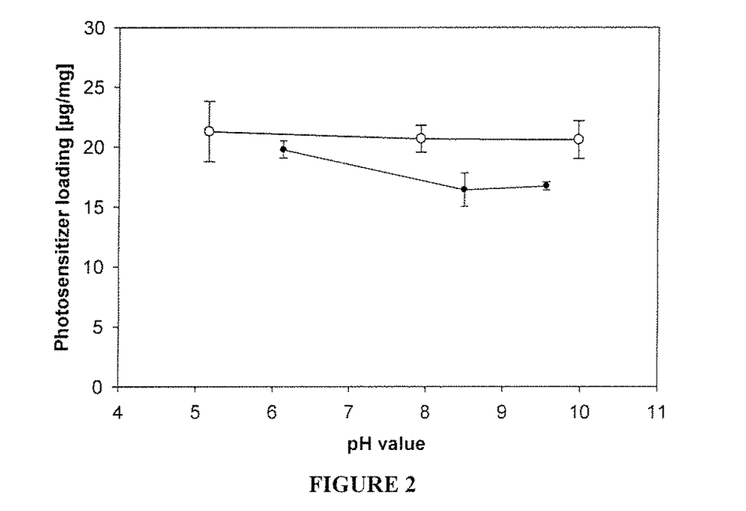
FIG. 2 Drug loading of HSA nanoparticles with Mthpp (○) and mTHPC (●) in the presence of 1.5% soluble HSA depending on the pH value in the range between 5 and 10 (mean±S.D.; n=3).

Typically 100 mg of HSA was dissolved in 1 ml of 10 mM sodium chloride solution. The pH was titrated to 8.0 and the solution was filtered through a 0.22 µm filtration unit (Schleicher and Schüll, Dassel, Germany). To 333.0 µL, of the purified HSA nanoparticle suspension (15 mg/ml) 56.3, 75.0, 93.8, 112.5, 131.3, and 150.0 µL (0.75-2.0%) of the resulting aqueous HSA solution were added, respectively. FIG. 1 illustrates the drug loading of HSA-based nanoparticles on the concentration of dissolved HSA in the system. The suspensions were adjusted to 500.0 µL with purified water followed by addition of 112.5 µL of an ethanolic mTHPP stock solution (ethanol 96% (V/V), 1 mg/ml) and 137.5 µL of ethanol 96% (V/V). Incubation was performed at pH values between 5 and 10 (See FIG. 2). The samples were incubated for 2 h under permanent shaking (15° C., 660 rpm). Particles were purified by repeated centrifugation at 20,817 g for 10 min at 15° C. and redispersed in 1 ml water in an ultrasonic bath for 5 min. In FIG. 2 drug loading of HSA based nanoparticles with mTHPP (○) and mTHPC (●) in the presence of 1.5% soluble HSA depending on the pH value in the range between 5 and 10 (mean±S.D.; n=3) has been illustrated. FIGS. 1 and 2 show, the drug loading of HSA-based nanoparticles is dependent on the concentration of HSA and its pH. The pH value can affect the drug loading.

All of the solutions used for particle preparation were sterile and pre-filtered through a membrane with a pore size of 0.22 µm. All of the equipment used was autoclaved at 121° C. over 20 min. All handling steps for particle preparation were performed under a laminar airflow cabinet. Thus, HSA-based nanoparticles of present invention are formulated under completely aseptic conditions ensuring production of sterilize nanoparticles for therapeutic use.

Figure 3:
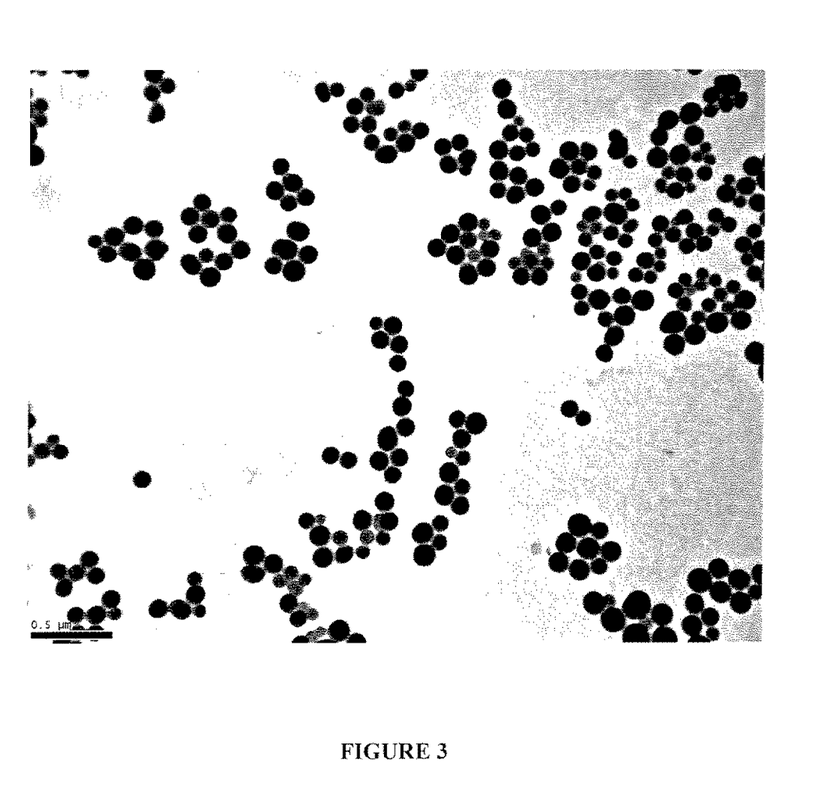
FIG. 3 Transmission electron microscopy image of mTHPP-loaded HSA nanoparticles prepared in the presence of 1.5% dissolved HSA in ethanol 34.3% (V/V) for drug adsorption process.
Figure 4:
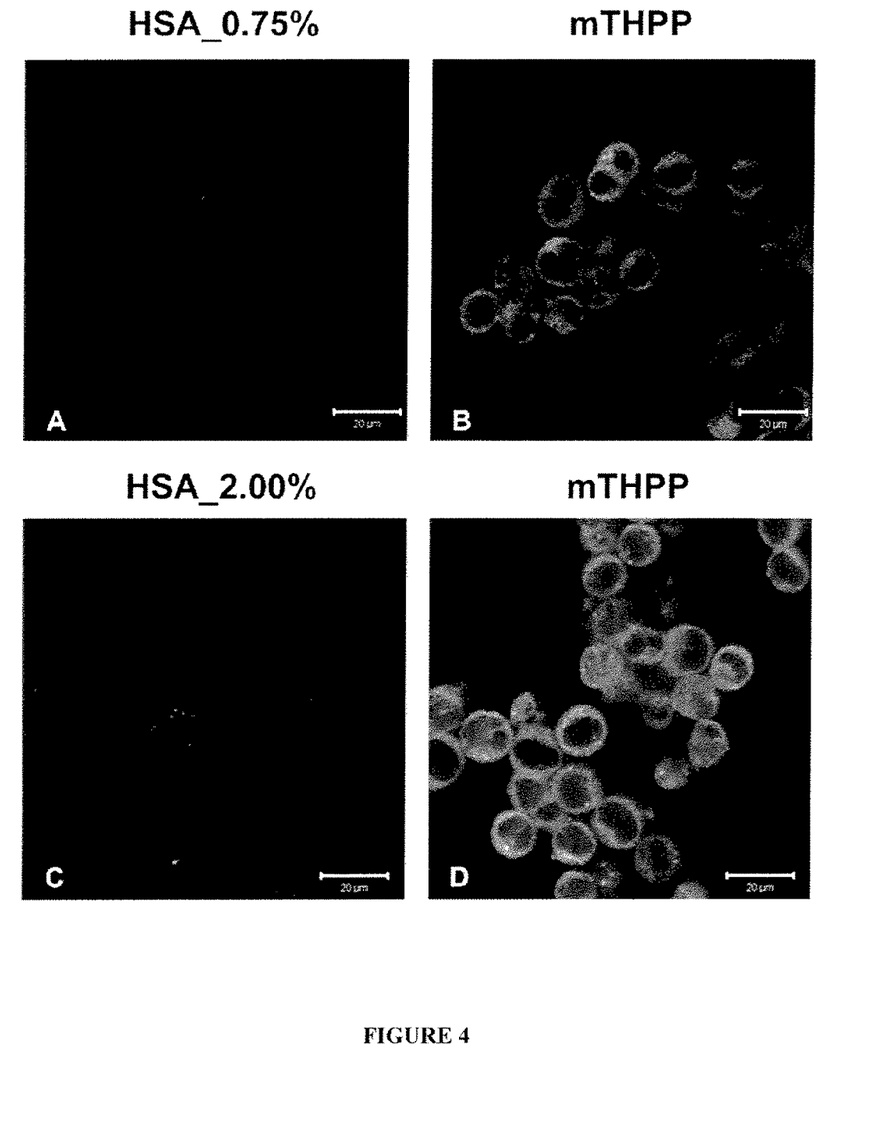
Figure 5:
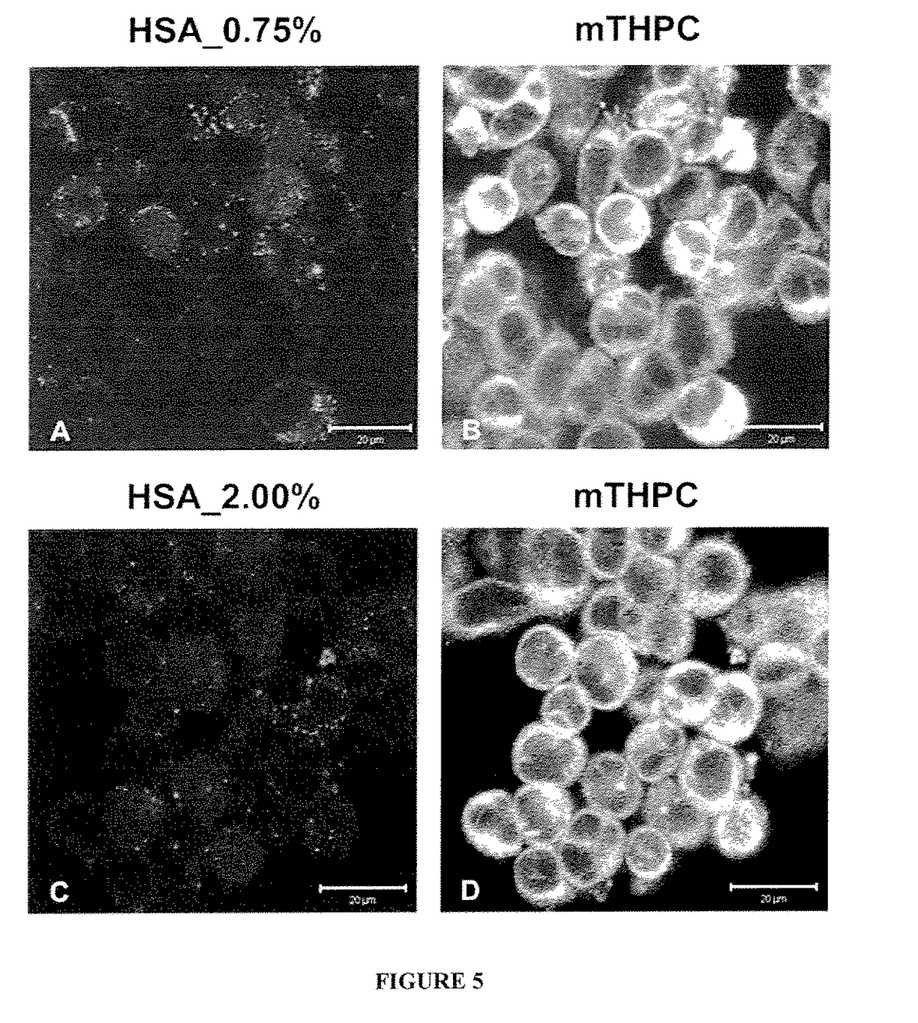

Average particle size and polydispersity were measured by photon correlation spectroscopy using a Zetasizer 3000HSA (Malvern Instruments, Malvern, UK). Nanoparticle content was determined by microgravimetry. Particle morphology was determined by transmission electron microscopy (TEM). FIG. 3 depicts the image produced by TEM of mTHPP-loaded HSA nanoparticles prepared in the presence of 1.5% dissolved HSA in ethanol 34.3% (V/V) for drug adsorption process.

Indirect quantification procedure: The mTHPP loading of the nanoparticles was calculated after spectrophotometric quantification of the unbound drug in the supernatants of the nanoparticles.

Direct quantification procedure: 10 mg pepsin were dissolved in 1 ml of an aqueous solution of 1% formic acid. An aliquot containing 1.0 mg photosensitizer loaded HSA nanoparticles was added to 250 µL of the pepsin solution. The mixture was adjusted to 500.0 µL by purified water. The samples were incubated for 2 h, under permanent shaking. After incubation 1.0 ml of ethanol 96% (V/V) was added followed by centrifugation of the solution (15° C., 20,817 g, 30 min). To 800.0 µl of the supernatant an amount of 200.0 µL of 50 mM bicarbonate buffer (pH=9) was added. The solution was measured photometrically at 512 nm for mTHPP (and 517 nm in case of mTHPC) to determine the content of photosensitizer attached to the purified nanoparticles.

Lyophilisation of the Nanoparticles can be Performed According to the Following Protocol:

For the freeze drying process trehalose was added at a concentration of 3% (m/V) to the nanoparticle samples. The samples were transferred to a freeze drier and the shelf temperature was reduced from 5° C. to −40° C. at a rate of 1° C./min. The pressure was set at 0.08 mbar. These parameters were maintained for 6 h. By increasing the temperature from −40° C. to −25° C. at 0.5° C./min the primary drying was achieved. The pressure remained unchanged. At the end of the primary drying heat ramp, a Pressure Rise Test (PRT) was performed. With termination of the primary drying the secondary drying followed by increasing the temperature at a rate of 0.2° C./min to 25° C. This temperature was held for 6 h at a pressure of 60 mT (=0.08 mbar).

Sterility of the nanoparticle preparations was proven according to the monograph 2.6.1 "Sterility" of the European Pharmacopoeia. The sterility test was performed by the direct inoculation method as described in the monograph.

Table I shows the physico-chemical characteristics of 5,10, 15,20-tetrakis(m-hydroxyphenyl)-porphyrin (mTHPP)-loaded HSA nanoparticles (mean±S.D.; n=6) prepared using the method described above.

Table III shows the lifetime of triplet state and singlet oxygen generated by the reference Rose Bengal and the photosensitizer loaded HSA nanoparticle preparations. Rose Bengal shows lifetime and quantum yield as it was described earlier by Redmond et al. (1999). While the quantum yield of the nanoparticles showed a decrease for both preparations, an increase in the lifetime of the reactive oxygen species was observed. The increase of singlet oxygen lifetime indicates that the photosensitizers are preserved in the monomeric form. Due to the hypoxic environment of the nanoparticle surface a decrease of the quantum yield could be expected. An increase of the singlet oxygen generation after degradation of the HSA nanoparticles and the release of the photosensitizer can be assumed.

TABLE I

Physico-chemical characteristics of mTHPP-loaded HSA nanoparticles (mean ± S.D.; n = 6)

| Parameter | Unloaded | 0.75% HSA | 1.0% HSA | 1.25% HSA | 1.5% HSA | 1.75% HSA | 2.0% HSA |
|---|---|---|---|---|---|---|---|
| Particle diameter [nm] | 189.9 ± 0.4 | 194.7 ± 6.4 | 197.0 ± 5.0 | 195.6 ± 3.0 | 204.0 ± 5.2 | 199.7 ± 14.3 | 203.0 ± 18.0 |
| Polydispersity | 0.045 ± 0.024 | 0.050 ± 0.001 | 0.026 ± 0.011 | 0.064 ± 0.016 | 0.009 ± 0.009 | 0.069 ± 0.009 | 0.086 ± 0.082 |
| mTHPP loading [µg/mg] | — | 21.6 ± 6.8 | 21.0 ± 7.0 | 21.1 ± 0.2 | 20.3 ± 1.0 | 18.6 ± 0.2 | 17.3 ± 0.3 |

Table II shows the fluorescent lifetimes of 5,10,15,20-tetrakis(m-hydroxyphenyl)-porphyrin (mTHPP)-loaded HSA nanoparticles prepared using the above method. Preparation was performed in the presence of 0.75% and 2.0% soluble HSA, respectively. The longest component $\tau_3$ is 8.2 ns, which is similar to that of the mTHPP monomers (9.6 ns). Such a slightly shortened lifetime has been reported for photosensitizers attached to large units, for instance, pheophorbide a coupled to dendrimers. The amplitude of $\tau_3$ exceeded 40% of the total fluorescence intensity of mTHPP loaded HSA nanoparticles. At the same time, the decay time $\tau_2$ with 2.1-2.3 ns shows an amplitude of about 25%. The shortest lifetime $\tau_4$ (0.35 ns) contributes with 32.9% to the whole fluorescence signal.

TABLE III

Singlet oxygen generation and triplet parameters of Rose Bengal in ethanol and in form of HSA nanoparticles mTHPP-loaded in the presence of 0.75% and 2.0% soluble HSA in aqueous solutions

| Samples | $\tau_T$ [µs] | $\tau_\Delta$ [µs] | $\Phi_\Delta$ (±0.03) |
|---|---|---|---|
| Rose Bengal | 3.3 ± 0.1 | 64.1 ± 0.2 | 0.75 |
| HSA nanoparticles 0.75% soluble HSA | 13.7 ± 0.2 | 149 ± 1 | 0.04 |
| HSA nanoparticles 2.0% soluble HSA | 8.0 ± 0.1 | 134 ± 1 | 0.03 |

TABLE II

Fluorescence lifetime of mTHPP in ethanol and in form of HSA nanoparticles mTHPP-loaded in the presence of 0.75% and 2.0% soluble HSA in aqueous solutions

| Samples | $\tau_1$ [ns] ± 0.05 | Amplitude [%] | $\tau_2$ [ns] ± 0.1 | Amplitude [%] | $\tau_3$ [ns] ± 0.2 | Amplitude [%] | $\chi^2$ |
|---|---|---|---|---|---|---|---|
| mTHPP in EtOH | — | — | — | — | 9.6 | 100 | 1.01 |
| HSA nanoparticles 0.75% soluble HSA | 0.29 | 28.7 | 2.1 | 25.8 | 8.2 | 45.5 | 0.97 |
| HSA nanoparticles 2.0% soluble HSA | 0.35 | 32.9 | 2.3 | 25.5 | 8.2 | 41.6 | 1.02 |

EXAMPLE 1b

Preparation and Characterization of HSA-Based Nanoparticles with the Photosensitizer mTHPC; Adsorptive Binding to Particle Surface (Table IV)

Nanoparticles were prepared according to example 1a with the exception that mTHPC was used instead of mTHPP.

mTHPC-loaded nanoparticles were characterized as described within example 1a. Table IV shows the physico-chemical characteristics of 5,10,15,20-tetrakis(m-hydroxyphenyl)-chlorin (mTHPC)-loaded HSA nanoparticles (mean±S.D.; n=3)

TABLE IV

Physico-chemical characteristics of mTHPC-loaded HSA nanopartides (mean ± S.D.; n = 3)

| Parameter | Unloaded | 0.75% HSA | 1.0% HSA | 1.25% HSA | 1.5% HSA | 1.75% HSA | 2.0% HSA |
|---|---|---|---|---|---|---|---|
| Particle diameter [nm] | 211.6 ± 5.7 | 200.4 ± 0.9 | 199.6 ± 0.8 | 199.0 ± 1.8 | 203.2 ± 2.2 | 208.2 ± 2.7 | 206.9 ± 3.6 |
| Polydispersity | 0.038 ± 0.008 | 0.043 ± 0.018 | 0.006 ± 0.004 | 0.044 ± 0.012 | 0.055 ± 0.018 | 0.016 ± 0.010 | 0.081 ± 0.062 |
| mTHPC loading [µg/mg] | — | 24.1 ± 0.5 | 25.2 ± 0.5 | 21.7 ± 1.9 | 23.2 ± 0.8 | 21.4 ± 2.3 | 24.2 ± 1.1 |

EXAMPLE 1c

Preparation and Characterization of HSA-Based Nanoparticles with the Photosensitizer mTHPC: Incorporative Binding Human serum albumin (HSA) based nanoparticles were prepared by a desolvation method using polyethylene glycol as desolvating agent. In principle, an amount of 90 mg HSA was dissolved in 0.9 ml of 10 mM sodium chloride solution. The pH was adjusted to 6-8 and the solution was filtered through a 0.22 µm filtration unit (Schleicher and Schüll Dassel, Germany). mTHPC was added in form of 0.1 ml ethanolic solution containing 3, 7.5, and 15 mg/ml mTHPC, respectively. After an incubation period of 15 min, nanoparticles were formed by continuous addition of 4.0 ml aqueous polyethylene glycol (PEG4000) solution under continuous stirring (400-500 rpm) at room temperature. A defined amount of ethanol is added at a rate of 1 ml/min using a pumping device (Ismatec IPN, Glattbrugg, Switzerland). After protein desolvation 78 µL (or 104, and 182 µl, respectively) of 8% aqueous glutaraldehyde solution were added to stabilize the resulting protein nanoparticles by chemical cross linking. The glutaraldehyde concentration used corresponds to 150% (or 200%, and 350%, respectively) stoichiometric cross linking of the amino groups in 90 mg HSA. Particles were stirred for 3 h and were purified by 3 cycles of centrifugation at the rate of 20,817 g, for 10 min) and redispersion in 1.0 ml water in an ultrasonic bath (5 min). The nanoparticle content was determined by microgravimetry and was adjusted to 15.0 mg/ml.

All of the solutions used for particle preparation were sterile filtered through a membrane with a pore size of 0.22 µm. All of the equipment used was autoclaved at 121° C. over 20 min. All handling steps for particle preparation were performed under a laminar airflow cabinet.

mTHPC-loaded nanoparticles were characterized as described within example 1a.

EXAMPLE 2a

Analysis of the Cell Uptake of HSA-based Nanoparticles with the Photosensitizer 5,10,15,20-tetrakis(3-hydroxyphenyl)-porphyrin (mTHPP) (FIGS. 4A-D)

To analyse the cellular uptake and the intracellular distribution of the HSA-based nanoparticles, the confocal laser scanning microscopy was used. DiFi cells were cultured on glass slides (Becton Dickinson) and incubated with the nanoparticulate formulation for 4 h at 37° C. Following, the cells were washed twice with PBS and the membranes were stained with Concanavalin A AlexaFluor350 (50 µg/ml: Invitrogen, Karlsruhe) for 2 min. Cells were fixed with 0.4% paraformaldehyde for 6 min. After fixation, the cells were washed and then embedded in Vectashield HardSet Mounting Medium (Axxora, Grünberg). The microscopy analysis was performed with an Axiovert 200 M microscope with a 510 NLO Meta device (Zeiss, Jena), a chameleon femtosecond or an argon ion laser and the LSM Image Examiner software. The green autofluorescence of the HSA based nanoparticles and the red autofluorescence of the photosensitizer 5,10,15,20-tetrakis(3-hydroxyphenyl)-porphyrin (mTHPP) were used to determine the distribution.

FIGS. 4A-D illustrate the cellular uptake and intracellular distribution of HSA based nanoparticles (0.75 and 2.00% soluble HSA) with the photosensitizer 5,10,15,20-tetrakis(3-hydroxyphenyl)-porphyrin (mTHPP) studied by confocal laser scanning microscopy. DiFi cells were cultured on glass slides and incubated with the nanoparticles for 4 h at 37° C. The red autofluorescence of the photosensitizer mTHPP and the green autofluorescence of the nanoparticles were used. Pictures were taken within inner sections of the cells. (FIG. 4A-B) Incubation of cells with HSA nanoparticles (0.75% soluble HSA) with mTHPP. (FIG. 4C-D) Incubation of cells with HSA nanoparticles (2.00% soluble HSA) with mTHPP. (FIG. 4A) and (FIG. 4C) display the green nanoparticle channel; (FIG. 4B) and (FIG. 4D) display the red photosensitizer channel. Scale bar=20 µm

EXAMPLE 2b

Cell Uptake and Cell Adhesion, Respectively, of HSA-based Nanoparticles with the Photosensitizer 5,10,15,20-tetrakis(3-hydroxyphenyl)-chlorin (mTHPC) (FIGS. 5A-D)

FIGS. 5A-D illustrate cellular uptake/adhesion and intracellular distribution of HSA based nanoparticles (0.75 and 2.00% soluble HSA) with the photosensitizer 5,10,15,20- tetrakis(3-hydroxyphenyl)-chlorin (mTHPC) studied by confocal laser scanning microscopy. DiFi cells were cultured on glass slides and incubated with the nanoparticles for 4 h at 37° C. The red autofluorescence of the photosensitizer mTHPC and the green autofluorescence of the nanoparticles were used. Pictures were taken within inner sections of the cells. (FIG. 5A-B) Incubation of cells with HSA nanoparticles (0.75% soluble HSA) with mTHPC. (FIG. 5C-D) Incubation of cells with HSA nanoparticles (2.00% soluble HSA) with mTHPC. (FIG. 5A) and (FIG. 5C) displays the green nanoparticle channel; (FIG. 5B) and (FIG. 5D) display the red photosensitizer channel. Scale bar=20° μm.

Samples were prepared according to example 2a with the exception that HSA-mTHPC was used instead of HSA-mTHPP.

EXAMPLE 3

Intracellular Uptake and Photodynamic Activity of the Photosensitizer-Loaded Nanoparticles Intracellular Uptake and Phototoxicity of mTHPC-HSA-Nanoparticles:

Intracellular uptake and phototoxicity of the present nanoparticles formulation was studied using Jurkat-cell suspensions cultured in RPMI1640 medium. All cells were incubated in 3 μM mTHPC and mTHPC loaded into different concentration of HSA based nanoparticles for set period of time (1 h, 3 h, 5 h, 24 h). The HSA-based nanoparticles of varying HSA concentration was used to determine the intracellular uptake and phototoxicity effect of the cells suspension.

Different sample of mTHPC-HSA-based nanoparticles having three different concentrations of HSA included:
  1 HSA 40% cross-linked with glutaraldehyde
  HSA 100% cross-linked with glutaraldehyde
  USA 200% cross-linked with glutaraldehyde The Jurkat-cell suspensions were incubated in five samples:
  1. Ref: No photosensitizer is added to the cell
  2. 3 μM mTHPC only
  3. HSA 40%-mTHPC-based nanoparticles
  4. HSA 100%-mTHPC-based nanoparticles
  5. HSA 200%-mTHPC-based nanoparticles Phototoxicity The Jurkat-cell suspensions incubated with the above mentioned five samples were irradiated at 660 nm for 2 min (using an LED), having a light dose of 290 ml/cm$^2$ to study the phototoxicity effect of cells.

Trypan blue test was used to assess the necrotic cells, apoptotic cells were detected by their change of cell shape (apoptotic blebbing).

FIGS. 6A-D depict dark toxicity and the phototoxicity effects on Jurkat cells in 5 different samples after different incubation times.

Figure 6:
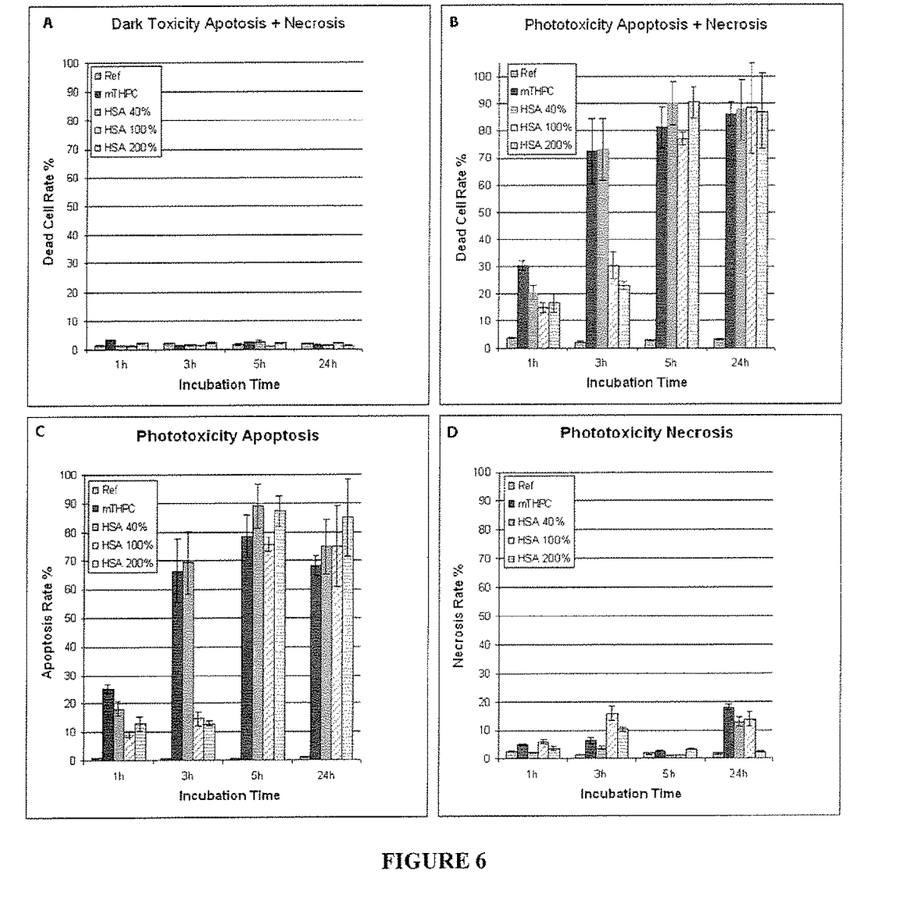

FIG. 6A illustrates the observed dark toxicity samples, where it was found to be almost zero indicating no toxic effect of the HSA-based nanoparticles. In each case Jurkat cells were incubated in five samples. After 1 h, 3 h, 5 h. and 24 h incubation in darkness an aliquot of each sample was investigated. Trypan blue test was used to assess the necrotic cells, apoptotic cells were detected by their change of cell shape (apoptotic blebbing). Little or no effect was found. In other words dark toxicity was not observed for the mTHPC concentrations used.

On the other hand, FIGS. 6B, 6C, 6D show apoptosis and necrosis effects, individually and together, on cells due to phototoxicity effect. FIG. 6C shows the rate of apoptosis, while FIG. 6D shows the rate of necrosis in the incubation medium separately; compared to FIG. 6B. The sample reference in each of FIGS. 6A-D represents the cells which were incubated and irradiated without photosensitizer. The cells were illuminated using a LED at 660 nm for an exposure time of 120 s and light dose of 290 mJ/cm$^2$. The experiments were repeated twice and for each measurement the cell number was counted three times two hours after light exposure to get average. Error bars represent the standard deviation of six measurements (n=6). FIGS. 6C and 6D illustrate the apoptosis and necrosis effect on cells due to phototoxicity respectively when incubated in 5 different samples after different incubation times as mentioned above. A formulation of present invention when used in PDT is seen to initiate a high amount of apoptosis—a patient, gentle kind of cell death and a lower amount of necrosis—a kind of cell death with high immune system response but needed in low dose to prevent tumor recovery.

Quantification of Intracellular Uptake of mTHPC and Different mTHPC Loaded HSA Nanoparticles

Jurkat-cell suspension in cell growth medium (RPMI1640) was incubated in 3 μM of mTHPC and different concentration of HSA encapsulating 3 μM of mTHPC based nanoparticles, for 1 h, 3 h, 5 h, 24 h. After incubation the cells were counted (using a haemacytometer), washed with phosphate buffer solution (PBS, 400 g, 3 min, 2×) and the cell pellet was stored and frozen overnight at −20° C. to disrupt the cell membranes. From these cells the mTHPC was extracted in ethanol using ultrasound (>5 min). The mTHPC concentration in the ethanol extract was determined via fluorescence intensity using a standard fluorescence series. For the calculation of intracellular concentration the diameter of the cells was assumed to be 10 μm.

Figure 7:
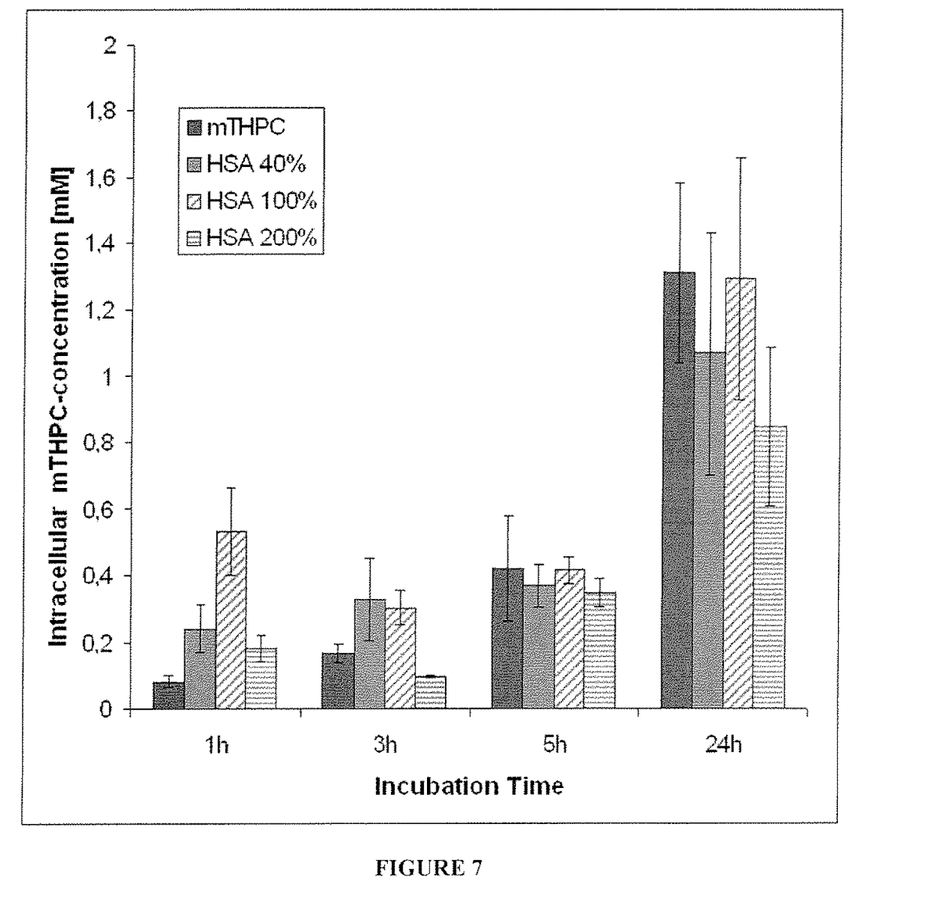
FIG. 7 Intracellular uptake of 3 µM in mTHPC, and different mTHPC-loaded HSA nanoparticles by Jurkat cells after different incubation times.

FIG. 7, shows the intracellular uptake of 3 μM, mTHPC, and different mTHPC loaded HSA nanoparticles by Jurkat cells after different incubation times. The experiments were repeated twice and for each measurement the cell number was counted three times to get average. Error bars represent the standard deviation of six measurements (n=6).

Having described preferred embodiments of the invention with reference to the accompanying drawings, it is to be understood that the invention is not limited to the precise embodiments, and that those skilled in the art can effect changes and modifications without departing from the scope of the invention as defined in the appended claims.

What is claimed is:

1. A nanoparticle pharmaceutical formulation for clinical use in photodynamic therapy comprising:
   human serum albumin based nanoparticles in a range of less than 500 nm in diameter;
   a therapeutically effective amount of a tetrapyrrole-based hydrophobic photosensitiror,
   a stabilizing agent;
   wherein said photosensitizes is a chlorin or bacteriochlorin derivative according to formula A wherein:
R¹ is: H or OH
R² to R⁵ are substituents either in the meta- or para position of the phenyl ring with R² to R⁵ independently of one another chosen from a group of substituents consisting of: —OH, —COOH, —NH₂, —COOX, —NHX, OX, —NH—Y—COOH, or —CO—Y—NH₂,
wherein:
  X is a polyethyleneglycol-residue with (CH₂CH₂O)ₙCH₃ with n=1-30 or a carbohydrate moiety
  Y is a peptides or oligopeptides wherein n=1-30,
  Ring D is having the structure:

wherein said stabilizing agent is selected from the group of typical stabilizers including glutaraldehyde, formaldehyde, and combinations of them; wherein said formulation is administered by parenteral means comprising intravenous injection; and wherein said drug loaded nanonarticles can be freeze dried in the presence of cryoprotective agents and reconstituted prior to injection.

2. The nanoparticle pharmaceutical formulation according to claim 1 wherein the therapeutically effective concentration of the photosensitizer is variable from 10 to 50 μg per milligram of HSA nanoparticle, which corresponds to a particle content of 5-25 mg/nil in water suspension.

3. The nanoparticle pharmaceutical formulation according to claim 1 wherein said photosensitizer is temoporfin.

4. The nanoparticle pharmaceutical formulation according to claim 1 wherein said photosensitizer is 2,3-dihydroxy-5,10,15,20-tetrakis(3-hydroxyphenyl)-chlorin (mTHPD-OH).

5. The nanoparticle pharmaceutical formulation according to claim 1 wherein said photosensitizer is 5, 10, 15, 20-tetralcis (3-hydroxyphenyl)-porphyrin (mTHPP).

6. The nanoparticle pharmaceutical formulation according to claim 1 wherein said cryoprotective agents are selected from the group of glucose, trehalose, sucrose, sorbitol, mannitol and combinations of them.

7. A method of preparation, under sterile conditions, of nanoparticle pharmaceutical formulation, according to claim 1, comprising the steps of:
  a. desolvating protein of an aqueous Human Serum Albumin solution containing sodium chloride and adjusted pH;
  b. filtering the solution through a filtration unit;
  c. stabilizing and purifying the resulting nanoparticles;
  d. loading the photosensitizer through adsorptive binding on particle surface, incorporative binding and combination of both.

8. The method of preparation according to claim 7, wherein the step of protein desolvation comprises a controlled addition of a hydrophilic organic solvent selected from the group of ethanol, methanol, isopropanol, acetone and combination of them.

9. The method of preparation according to claim 7, wherein the step of protein desolvation comprises the addition of concentrated polyethylene glycol solutions.

10. The method of preparation according to claim 7, wherein the stabilizing step comprises at least one thermal process, and uses at least one stabilizing agent.

11. The nanoparticle pharmaceutical formulation of claim 1 wherein the photosensitizer is selected from the group consisting of mTHPC, mTHPD-OH and mTHPP.

* * * * *